US007291473B2

(12) United States Patent
Tan et al.

(10) Patent No.: US 7,291,473 B2
(45) Date of Patent: Nov. 6, 2007

(54) SCREENING PROCESS FOR ATOPIC DERMATITIS

(75) Inventors: Eng M. Tan, La Jolla, CA (US);
Robert L. Ochs, Pittsburgh, PA (US);
Edward K. L. Chan, Gainesville, FL (US); Yoshinao Muro, Showa-Ku (JP)

(73) Assignee: The Scripps Research Institute, La Jolla, CA (US)

(*) Notice: Subject to any disclaimer, the term of this patent is extended or adjusted under 35 U.S.C. 154(b) by 324 days.

(21) Appl. No.: 10/276,919

(22) PCT Filed: May 23, 2001

(86) PCT No.: PCT/US01/16639

§ 371 (c)(1),
(2), (4) Date: Apr. 24, 2003

(87) PCT Pub. No.: WO01/90751

PCT Pub. Date: Nov. 29, 2001

(65) Prior Publication Data

US 2003/0215875 A1 Nov. 20, 2003

Related U.S. Application Data

(60) Provisional application No. 60/207,141, filed on May 23, 2000.

(51) Int. Cl.
*G01N 33/53* (2006.01)
(52) U.S. Cl. ............... 435/7.1; 435/7.92; 435/7.94; 435/960; 435/971; 436/506; 436/507; 436/518; 436/538; 424/130.1
(58) Field of Classification Search ............ 435/7.1, 435/7.92, 7.94, 960, 971; 436/506, 507, 436/512, 513, 518, 538; 424/130.1
See application file for complete search history.

(56) References Cited

U.S. PATENT DOCUMENTS

2005/0042631 A1* 2/2005 Ge ........................... 435/6

OTHER PUBLICATIONS

Quinti, et al., "Circulating IgG autoantibodies to IgE in atopic syndromes", *J. Allergy Clin. Immunol. 77*: 586-594 (1986).
Tada, et al., "Antinuclear Antibodies in Patients with Atopic Dermatitis and Severe Facial Lesions", *Dermatology 189*: 38-40 (1994).
Cooper, "Atopic Dermatitis: Recent Trends in Pathogenesis and Therapy", *J. Invest. Dermatol. 102*: 128-137 (1994).
Ochs, et al. "Autoantibodies in Interstitial Cystitis", *J. Urol. 151*: 587-592 (1994).
Radic, et al., "Genetic and Structural Evidence for Antigen Selection of Anti-DNA Antibodies", *Annu. Rev. Immunol. 12*: 487-520 (1994).

Konstantinov, et al., "Autoantibodies to Nuclear Envelope Antigens in Chronic Fatigue Syndrome", *J. Clin. Invest. 98*: 1888-1896 (1996).
Marone, et al., "The anti-IgE/anti-FcεRIα autoantibody network in allergic and autoimmune diseases", *Clinical and Experimental Allergy 29*: 17-27 (1999).
Valenta, et al., "Autoallergy: A Pathogenic Factor in Atopic Dermatitis?", *Curr. Prob. Dermatol. 28*: 45-50 (1999).
Seiberler, et al., "Characterization of IgE-Reactive Autoantigens in Atopic Dermatitis", *Int. Arch. Allergy Immunol. 120*: 108-116 (1999).
Tan, "Autoantibodies in Diagnosis and in Identifying Autoantigens", *The Immunologist 7*: 85-92 (1999).
Beltrani, "Atopic dermatitis: An update", *J. Allergy Clin. Immunol. 104*: S85-S86 (1999).
Beltrani, "The clinical spectrum of atopic dermatitis", *J. Allergy Clin. Immunol. 104*: S87-S98 (1999).
Leung, "Pathogenesis of atopic dermatitis", *J. Allergy Clin. Immunol. 104*: S99-S108 (1999).
Hayashi, et al., "Detection of anti-IgE and anti-FcεRI α chain auto-antibodies in patients with atopic dermatitis", *Allergology International 49*: 47-54 (2000).
Ochs, et al., "Autoantibodies to DFS 70 kd/transcription coactivator p75 in atopic dermatitis and other conditions", *J. Allergy Clin. Immunol. 105*: 1211-1220 (2000).
Muro, "Autoantibodies in atopic dermatitis", *J. Dermatol. Science 25*: 171-178 (2001).
Hanifin et al., "Diagnostic features of atopic dermatitis." *Acta Dermatovener (Stockholm) Suppl* 1980; 92:44-47.
Taniguchi, et al., "Positive antinuclear antibody in atopic dermatitis." *Acta Derm Venereo (Stockh) Suppl* 1992:176:62-64.
Gillenwater et al., "Summary of the National Institute of Arthritis, Diabetes, Digestive and Kidney Diseases Workshop on Interstitial Cystitis, National Institutes of Health, Bethesda Maryland Aug. 28-29, 1987," *J Urol* 1988; 140:203-206.
Koziol et al., "The natural history of interstitial cystitis: a survey of 374 patients," *J Urol* 1993; 149:465-469.
Ochs et al., *Interstitial Cystitis*, 1997, pp. 47-52.
Valenta et al., "Immunoglobulin E response to human proteins in atopic dermatitis," *J Invest Dermatol* 1996; 107:203-208.
Ge et al., "Purification, cloning, and characterization of a human co-activator, PC4, that mediates transcriptional activation of Class II genes," *Cell* 1994; 78;513-522.

(Continued)

*Primary Examiner*—Bao-Thuy L. Nguyen
(74) *Attorney, Agent, or Firm*—Hugh Wang; Michael J. McCarthy; Thomas Fitting (57) ABSTRACT

The present invention provides a process of screening patients for atopic dermatitis. The process includes the step of determining, in sera of the patient, the presence of antibodies against nuclear antigens such as transcription co-activator p75, wherein the presence of such antibodies indicates atopic dermatitis. The screening process can be used to detect atopic dermatitis in patients suffering from other conditions such as asthma or interstitial cystitis.

6 Claims, 2 Drawing Sheets

OTHER PUBLICATIONS

Ge et al., "Isolation of cDNAs encoding novel transcription coactivators p52 and p75 reveals an alternate regulatory mechanisms of transcriptional activation," *EMBO J.* 1998; 17:6723-6729.

Ochs et al., "6th International Congress on Cell Biology and 36th American Society for Cell Biology Annual meeting," *Molec Biol Cell* 1996; 6.75a Suppl.

Singh et al., "The role of the p53 protein in the selective vulnerability of the inner retina to transient ischemia," *Invest Ophthalmol Vis Sci* 1998; 39(11):2132-9.

Tan, "Autoantibodies in pathology and cell biology," *Cell* 1991; 67:841-842.

Forrest et al., "Identifying genes predisposing to atopic eczema," *J Allergy Clin Immunol* 1999; 104:1066-1070.

Fagerholm et al., "Atopic cataract: changes in the lens epithelium and subcapsular cortex," *Graefes Arch Clin Ophthamol.* 1984; 221:149-152.

Nakano et al., "Ocular complications of atopic dermatitis," *J Jpn Ophthalmaol Soc* 1997; 101:64-68 (abstract).

* cited by examiner

SCREENING PROCESS FOR ATOPIC DERMATITIS

Funds used to support some of the studies reported herein were provided by the National Institutes of Health (NIH grants DK49413 and AR32063). The United States Government may, therefore, have certain rights in any invention disclosed herein.

TECHNICAL FIELD OF THE INVENTION

The field of this invention is diagnosis of atopic dermatitis.

BACKGROUND OF THE INVENTION

Atopic dermatitis (AD) is a chronic, relapsing, pruritic skin disorder that generally first appears in childhood and frequently progresses to asthma and/or allergic rhinitis in the adult (Hanifin et al., *Acta Dermatovener (Stockholm) Suppl* 1980; 92:44-47; Leung et al., *Dermatology in General Medicine*, 4th edition, 1993, pp. 1543-1564; Cooper, *J Invest Dermatol* 1994; 102:128-137). There are no reliable laboratory markers for this condition but AD patients often have elevated serum IgE levels, allergic reactivity to foods and to other common allergens such as pollens, molds, and insects. There have also been reports of antinuclear antibodies (ANAs) in this condition (Taniguchi et al., *Acta Derm Venereol (Stockh) Suppl* 1992; 176:62-64; Tada et al., *Dermatol* 1994; 189:38-40). The prevalence of AD appears to be on the rise, with 10-15% of the population being affected at some time during childhood (Beltrani, *J Allergy Clin Immunol* 1999; 104:587-598; Leung, *J Allergy Clin Immunol* 1999; 104: S99-S108). We now report the finding of an autoantibody-autoantigen system in 30% of patients with AD which is also shared to a lesser extent by patients with asthma and interstitial cystitis (IC). IC is a urinary bladder condition in which the classical pathology is characterized by predominant mononuclear cell infiltration of the lamina propria with lymphocytes, plasma cells and mast cells (Gillenwater, et al., *J Urol* 1988; 140:203-206).

BRIEF SUMMARY OF THE INVENTION

The present invention provides a process of screening patients for atopic dermatitis. The process includes the step of determining, in sera of the patient, the presence of antibodies against nuclear antigens such as transcription co-activator p75, wherein the presence of such antibodies indicates atopic dermatitis. The screening process can be used to detect atopic dermatitis in patients suffering from other conditions such as asthma or interstitial cystitis.

In accordance with the process, sera is obtained from the patient and contacted with the nuclear antigen (e.g., nuclear transcription co-activator p75). The resulting mixture is maintained for a period of time sufficient for formation of an immune complex between antibodies in the sera and the antigen. The antibodies can be of the IgG or IgE class of immunoglobulins.

BRIEF DESCRIPTION OF THE DRAWINGS

FIG. 1 (shown in two panels designated 1A and 1B) shows the cloning and sequence data for DFS70. Panel 1A is a schematic representation of overlapping cDNAs. Clone 6.1 was obtained by immunoscreening a T24 cDNA library with a human anti-DFS serum and clone 52 by 5' RACE. The combined cDNA represented 3117 nucleotides. Panel 1B shows the nucleotide (SEQ ID NO:1) and deduced amino acid (SEQ ID NO:1) sequences of DFS-70. Sequencing of both DNA strands was performed with custom synthetic oligonucleotide primers. The open reading frame starts at nucleotide 54 and ends at nucleotide 1645. The methionine start sequence and the polyadenylation signals AATAAA/ATTAAA are underlined. The combined nucleotide and amino acid sequences for the original clone 6.1, starting at nucleotide 593 and ending at nucleotide 3117, were submitted to GenBank under accession number U94319 in March 1997. The differences in nucleotides between DFS70 and p75 (residues single underlined) are at position 726 a→t (Glu→Gly) and 1314 a→t (Tyr→Phe) while there were no differences between DFS70 and LEDGE (lens epithelium derived growth factor) at these positions. DFS70 differed from both p75 and LEDGF (residues double underlined) at position 188 g→t (Val→Phe), 244 g→a (no aa change) and 347 a→g (Thr→Ala).

DETAILED DESCRIPTION OF THE INVENTION

The present invention provides a process of screening patients for atopic dermatitis. The process includes the step of determining, in sera of the patient, the presence of antibodies against nuclear antigens such as transcription co-activator p75, wherein the presence of such antibodies indicates atopic dermatitis. The screening process can be used to detect atopic dermatitis in patients suffering from other conditions such as asthma or interstitial cystitis.

The identification of an antigen-antibody system in AD was initiated by an observation in IC patients of an autoantibody against a nuclear antigen distributed as dense fine speckles in the nucleoplasm of cells in interphase and increased localization in condensed chromosomes in mitosis. In addition, in immunoblotting using tissue culture extract as the antigen source, sera of such patients reacted with a 70 kilodalton (kDa) protein. This antigen was called DFS-70, incorporating the immunolocalization of the antigen (dense fine speckles) and the estimated molecular size of the antigen in polyacrylamide-SDS gels (Ochs et al., *J Urol* 1994; 151:587-592). The antibody was present in higher frequency in AD patients than in IC patients. This antigen is a nuclear protein, which is identical to a nuclear transcription co-activator called p75. The antibody is also present in other conditions and it is likely that the underlying common feature is the presence of AD in patients with asthma, interstitial cystitis and other disease states.

In accordance with the process of this invention, sera is obtained from a patient suspected on having AD. The sera is contacted with the nuclear antigen (e.g., nuclear transcription co-activator p75). The resulting mixture is maintained for a period of time sufficient for formation of an immune complex between antibodies in the sera and the antigen. The antibodies can be of the IgG or IgE class of immunoglobulins. Means for collecting sera from patients are well known in the art. Determination of immune complex formation can be accomplished by any means known in the art. A specific example of such determination is set forth herein below.

The following teaching discloses a particular embodiment of this invention. A skilled artisan will readily recognize that other embodiments can be used. Thus, the particular teachings set forth below are not limiting of the specification and claims in any way.

Patients and Antibody Controls

Sixty-four patients with atopic dermatitis, from the Department of Dermatology, Nagoya University School of Medicine, Nagoya, JAPAN, were enrolled in our study. Diagnostic criteria for AD were those described by Hanifin and Rajka (Hanifin et al., *Acta Dermatovener (Stockholm) Suppl* 1980; 92:44-47). Chart records were reviewed for age, sex, duration of disease, eosinophil numbers, IgE levels, presence of respiratory atopy (bronchial asthma, allergic rhinitis), and a degree of facial dermatitis. Patients with interstitial cystitis were diagnosed using established criteria (Gillenwater et al., *J Urol* 1988; 140:203-206) and were part of a large study on clinical features and sero-epidemiology reported previously (Koziol et al., *J Urol* 1993; 149:465-469; Ochs et al., *Interstitial Cystitis* 1997, pp.47-52).

Patients with asthma were recruited from the Division of Allergy and Immunology, Scripps Clinic, La Jolla and fulfilled the American Thoracic Society criteria for the diagnosis of asthma. Psoriasis patients without accompanying atopic dermatitis came from a clinical practice. Patients with chronic fatigue syndrome were reported and characterized in a previous study (Konstantinov et al., *J Clin Invest* 1996; 98:1888-1896). Normal human sera and sera from patients with systemic lupus erythematosus, rheumatoid arthritis, Sjögren's syndrome, and scleroderma were obtained from the serum bank of the W. M. Keck Autoimmune Disease Center, Scripps Research Institute, La Jolla, Calif.

Immunofluorescence

Sera from patients and controls were diluted ⅟₁₀₀ in PBS and examined by indirect immunofluorescence for the presence of autoantibodies to nuclear and cytoplasmic antigens on commercially prepared HEp-2 cell substrate slides (Bion, Park Ridge, Ill.) with anti-human IgG coupled to FITC (Caltag, San Francisco, Calif.) as the secondary detecting reagent. IgG subclass identification of autoantibodies was performed by indirect immunofluorescence on commercially prepared HEp-2 cell substrate slides as described above using affinity-purified FITC-conjugated sheep anti-human IgG1, IgG2, IgG3, and IgG4 (The Binding Site, Birmingham, England) as secondary antibodies.

Immunoblotting

Human MOLT-4 cells (a T cell line) were obtained from the American Type Culture Collection (Rockville, Md.) and grown in suspension culture in RPMI-1640 supplemented with 10% fetal bovine serum, 2 mM L-glutamine and 10 μg/ml gentamicin sulfate. Whole-cell extracts were prepared from MOLT-4 cells by pelleting suspended cells in media, rinsing in PBS, and resuspending the cell pellet in an equal volume of 2× gel electrophoresis sample buffer containing a cocktail of protease inhibitors (catalog #1697498, Boehringer Manmheim, Indianapolis, Ind.). The cell extract was then sonicated on ice for 4-5 bursts of 10 sec. each until the cells were dispersed. After sonication, the extract was then passed through progressively finer gauge needles, from #18 to #27, to shear the DNA and then the extract was boiled for 5 min., centrifuged to remove insoluble material, and aliquots stored at −70° C. This form of cell extract has been used extensively in many previous studies (Ochs et al., *Interstitial Cystitis* 1997, pp.47-52; Konstantinov et al., *J Clin Invest* 1996; 98:1888-1896) as a source of autoantigens for detection of serum autoantibodies against ubiquitous cellular antigens.

Western blotting was performed essentially as described by Chan and Pollard (Chan et al., *Manual of Clinical Laboratory Immunology* 1992, pp.755-762). Serum was diluted ⅟₁₀₀ and detection of immunoreactive bands was performed by chemiluminescence using peroxidase-conjugated goat anti-human IgG (Caltag, Burlingame, Calif.) and the ECL chemiluminescence kit (Amersham, Arlington Heights, Ill.) according to the manufacturer's directions, followed by autoradiography. For blotting of recombinant DFS70, the detection procedure was identical.

For detection of specific IgE autoantibodies to DFS70, serum samples were diluted ⅟₁₀ according to Valenta et al. (Valenta et al., *J Invest Dermatol* 1996; 107:203-208) in order to detect serum IgE levels that are on average 100,000 times lower in amount compared to levels of IgG. IgE antibody was detected using peroxidase-conjugated goat IgG antibody to human IgE epsilon heavy chain (Cappel, Durham, N.C.) as the secondary detecting reagent, followed by chemiluminescence and autoradiography as described above for the detection of IgG. Normal control sera were included in every determination in order to exclude spurious findings in tlis procedure.

cDNA Cloning

DFS70 was originally described using autoantibodies from patients with interstitial cystitis (Ochs et al., *J Urol* 1994; 151:587-592) and was given the designation because of a characteristic immunohistochemical staining pattern on HEp-2 (human epithelial Line) cells consisting of dense fine specldes distributed in the nucleoplasm in interphase cells and with accentuated generalized staining of condensed chromosomes in mitotic cells. These sera also showed reactivity with a 70 kDa protein in MOLT-4 extracts in Western blotting. One of these sera, which was high in antibody titer and available in larger quantity, was used to isolate a partial cDNA sequence as indicated below.

The method for primary screening of a T24 (bladder carcinoma cell line) cDNA expression library was reported previously (Ochs et al., *Molec Biol Cell* 1996; 7:1015-1024). Briefly, serum from patient 90-49 was diluted ⅟₁₀₀ and preabsorbed with wild-type λ Zap Express phage without inserts. The preabsorbed serum was then used to screen approximately 300,000 recombinant plaques from a cDNA expression library constructed from T24, a bladder epithelial cell line (ATCC, Rockville, Md.), using $^{125}$I-staph protein A according to the method of Young and Davis (Young et al., *Proc Natl Acad Sci (USA)* 1983; 80:1194-1198). All screenings were carried out on duplicate filters and two double-positive clones were obtained. After multiple rescreening, clone DFS6.1 was amplified, purified, and used for sequence analysis. Clone DFS6.1 was a partial cDNA and in order to isolate full-length cDNA multiple overlapping 5' clones were obtained from human placenta cDNAs using a modified 5'-RACE method previously described (Lung et al., *Trends Genet.* 1996; 12:389-391). Clone DFS6.1 was reported in an abstract (Ochs et al., *Molec Biol Cell* 1995; 6:75a Suppl.) and the nucleotide sequence was submitted to Gen Bank under accession No. U94319 in March 1997.

Sequence and Protein Anaylses cDNA inserts were analyzed by restriction mapping and sequencing. Nucleotide sequence was determined by dye primer cycle sequencing using a Model 373A DNA sequencer from Applied Biosystems (ABI, Foster City, Calif.). Oligonucleotide primers were synthesized with a Model 394 DNA synthesizer (ABI). DNA and protein sequences were analyzed by the Genetics Computer Group (GCG) Sequence Analysis Software Package version 7.2 for UNIX computers (Deveraux et al., *Nucleic Acids Res* 1984; 12:387-395). Alignment of protein sequences was achieved with the GAP program that employed the algorithm of Needleman and Wunsch. Molecular mass was calculated using the GCG program PEPTIDESORT.

Purification of Recombinant DFS70

For expression and purification of recombinant protein, the EcoR1-EcoR1 fragment of clone DFS6.1 and the fall-length cDNA were subcloned into pET 28 vector (Novagen, Madison, Wis.). The full-length cDNA was obtained by RT-PCR using T24 cell mRNA and primers corresponding to sequences flanking the methionine start codon and 3' stop codon. The sense and antisense primers were 5'-GCA GAATTCGATACATGACTCGCGATTTC-3' (SEQ ID NO:3) and 5'-AGTG AAGCTTATATTCCAGGTATGTCAACCTACGTT-3' (SEQ ID NO:4) and the sequences incorporated to facilitate subdloning were EcoRI and HindIII restriction sites. The pET28 vector has N-terminal fusion tags comprising T7 and 6× histidine. The T7 fusion tag allows for easy detection of recombinant protein with T7 antibodies and the 6 × histidines allow for protein purification due to the high affinity of histidine to nickel. $E.\ coli$ strain BL21-DE3 containing the pET 28a vector with the DFS6.1 insert was grown in LB media containing kanamycin until $OD_{600}$=0.8. Then, 5 mM IPTG was added to induce recombinant protein expression for 6 hrs. at 37° C. Cells were harvested by centrifugation and broken open by cycles of freezing and thawing in a buffer solution containing 6M guanidine hydrochloride according to the manufacturer's directions (Qiagen, Chatsworth, Calif.). This solution was then passed through a Ni-NTA-Agarose resin (Qiagen, catalog #30210) column where the recombinant protein is bound at elevated pH (pH 8.0) by the affinity of nickel for the 6 x His portion, unbound material washed out, and the recombinant protein eluted in fractions at a pH of 6.0. Each fraction was checked by Western blotting for the presence and purity of recombinant protein.

Recombinant Proteins and Antibodies for Transcription Coactivators p52 and 75

The USA (upstream stimulatory activity) fraction of HeLa cells containing the transcription coactivator proteins p52 and p75 was described previously (Ge et al., Cell 1994; 78:513-523). Subsequent studies resulted in the cDNA cloning and production of recombinant proteins for p52 and p75 and the production of rabbit polyconal antibodies (Ge et al., EMBO J. 1998; 17:6723-6729). These reports appeared while these studies were in progress and it was noted that our plasmid DFS 6.1 had complete identity with the corresponding region of p75. Studies were therefore initiated with Ge and colleagues (NIH, Bethesda, Md.) and reagents exchanged to determine the reactivity of autoantibodies to p75 and p52 as described below.

Immunoelectron Microscopy

Small pieces of mouse intestine were fixed for 1 hr. at 4° C. with 1% glutaraldehyde buffered in PBS. Pieces were then dehydrated in 70% ethanol and embedded in LR White. After polymerization at 56° C. for 2 days, sections were collected grids. For immunolabeling, individual grids (with sections down) were incubated for 30-60 min. with a blocking solution consisting of 2% NGS/0.2% BSA made in Tris-buffered saline (TBS) containing 1.0% Tween-20 (0.02 M Tris, 0.15 M Na Cl, 1.0% Tween-20, pH 7.6). Grids were then transferred to drops consisting of a 1/100 dilution of human anti-DFS70 made in TBS/Tween-20 for 1 hr. at R. T. and then rinsed with TBS/Tween-20 10×1 min. each. Grids were then blocked for 30-60 min. in TBS/Tween-20 and incubated for 1 hr. at R. T. in a 1/50 dilution of goat anti-human IgG linked to 10 nm colloidal gold (Amersham) diluted in TBS/Tween-20. Grids were then rinsed in TBS/Tween-20 10×1 min. each, rinsed in PBS, fixed 30 min. at R. T. in 1% glutaraldehyde/PBS, rinsed in PBS 3×5 min., rinsed in distilled water 3×5 min, counterstained with uranyl acetate and lead citrate, rinsed in distilled water, and blotted dry.

ANAs in Patients with Atopic Dermiatitis

Sixty-four AD patients, 30 males and 34 females, were analyzed for IgG autoantibodies to nuclear antigens (abbreviated as antinuclear antibody [ANA]) by indirect immunofluorescence on commercial human HEp-2 cell substrates and by Western blotting on whole-cell extracts of human MOLT-4 cells (FIG. 1). AD patients ranged in age from 4-43 yrs. (average of 24.4 yrs.) and the duration of disease ranged from 1-35 yrs. (average 13.4 yrs.). Of these 64 AD patients, 26 (40.6%) had ANAs of one pattern or another but only 18 (28%) produced a pattern of dense fine-speckles in interhase nucleoplasm and staining of chromosomes in mitotic cells.

TABLE 1

Clinical and Laboratory Data on 18 Atopic Dermatitis Patients with DFS70-Staining Pattern in Immnunobistochemistry

| Patient | Sex | Age[a] | Dur.[b] | Eos[c] | IgE[d] | R.A.[e] | F.D.[f] | Antinuclear Antibodies | | Anti-DFS70[i] |
|---|---|---|---|---|---|---|---|---|---|---|
| | | | | | | | | Pattern[g] | Titer[h] | |
| 6 | F | 20 | 15 | ND | ND | BA/AR | yes | DFS/chr | 1280 | pos |
| 8 | F | 4 | 2 | 400 | 67 | no | yes | DFS/chr | >1280 | pos |
| 10 | F | 23 | 22 | 289 | 1859 | No | Yes | DFS/chr | 320 | pos |
| 12 | M | 19 | 14 | 1463 | 13226 | BA/AR | yes | DFS/chr/NBs | 640 | pos |
| 13 | F | 20 | 16 | 659 | 4224 | BA/AR | yes | DFS/chr | 640 | pos |
| 15 | F | 29 | 14 | 1440 | 65 | no | yes | DFS/chr/No | >1280 | pos |
| 16 | F | 22 | 13 | 566 | 6900 | no | yes | DFS/chr | 320 | neg |
| 28 | M | 23 | 23 | 629 | 5024 | AR | yes | DFS/chr | 320 | pos |
| 36 | F | 20 | 6 | 213 | 488 | AR | yes | DFS/chr | 1280 | pos |
| 38 | F | 15 | 7 | 743 | 2189 | no | yes | DFS/chr | 320 | pos |
| 39 | F | 20 | 20 | 1296 | 6270 | AR | yes | DFS/chr | 1280 | pos |
| 41 | F | 19 | 9 | 885 | 196 | no | yes | DFS/chr/NBs | 640 | pos |
| 68 | F | 20 | 8 | 568 | 1579 | no | yes | DFS/chr | 640 | pos |
| 77 | F | 27 | 26 | 975 | 1891 | no | no | DFS/chr | ND | neg |
| 78 | M | 21 | 9 | 87 | 1714 | no | yes | DFS/chr | ND | neg |
| 81 | M | 26 | 10 | 205 | 25 | no | no | DFS/chr | 320 | pos |

TABLE 1-continued

Clinical and Laboratory Data on 18 Atopic Dermatitis Patients with DFS70-Staining Pattern in Immnunohistochemistry

| Patient | Sex | Age[a] | Dur.[b] | Eos[c] | IgE[d] | R.A.[e] | F.D.[f] | Antinuclear Antibodies Pattern[g] | Titer[h] | Anti-DFS70[i] |
|---|---|---|---|---|---|---|---|---|---|---|
| 88 | F | 19 | 3 | 300 | 84 | AR | yes | DFS/chr/NBs | 640 | pos |
| 99 | F | 32 | 27 | 152 | 272 | AR | yes | DFS/chr | 640 | neg |

[a]Age in years
[b]Duration of disease in years
[c]Eosinophils/ml of blood
[d]IgE levels in IU/ml of blood
[e]Respiratory Atopy - BA, broncial asthma; AR, allergic rhinitis
[f]Facial dermatitis
[g]DFS, dense fine speckled staining; chr, mitotic chromosome staining; NBs, staining of unidentified nuclear bodies; No, nucleolar staining
[h]Titer of ANA; ND, not done
[i]Western blotting against recombinant DFS70; pos, positive; neg, negative The prototypic immunofluorescence staining pattern AD sera shows that interphase cell nuclei display fine specldes distributed in the nucleoplasm and aggregation of the specldes in the region of condensed chromosomes hi mitotic cells. A prototypic IC serum showed a similar pattern. Thirteen of the 18 patients described in Table 1 were included in the Western blot analysis depicting the initial studies, which showed that the majority of patients with DFS type antibodies appeared to be reacting with an antigen of approximately 70 kDa contained in MOLT-4 cell extracts. Lanes 5 to 22 consisted of 13 sera from patients in Table 1 with the addition of 5 other AD patients who did not have the distinctive DFS type of autoantibodies and other control positive and negative sera in lanes 1 to 4. It was noted that some AD sera had antibodies to antigens of other molecular sizes but the important finding was the occurrence of a common antigen-antibody system in the majority of sea with DFS-type antibodies. The last column of Table 1 includes data on the 18 DFS sera with respect to antibodies to recombinant antigen which is described firrther below. It should be noted from Table 1 that there was no significant relationship between the presence anti-DFS-70 antibody and parameters of age, duration of disease, eosinophils and IgE levels or with respiratory atopy but the majority of patients had facial dermatitis.

cDNA Cloning of DFS70: Sequence Identity to tite Transcriptional Co-activator p75

Figure 1A:
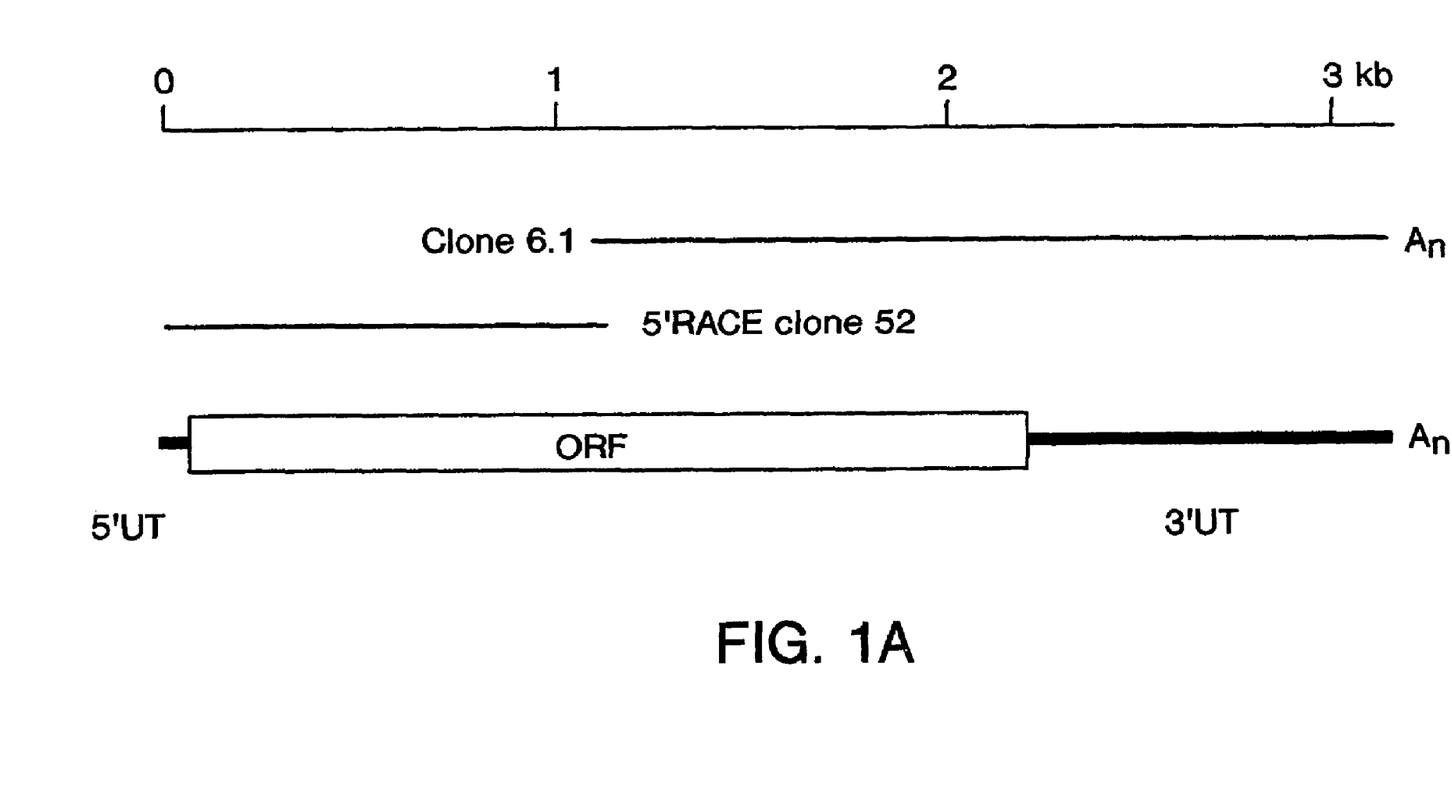
Figure 1B:
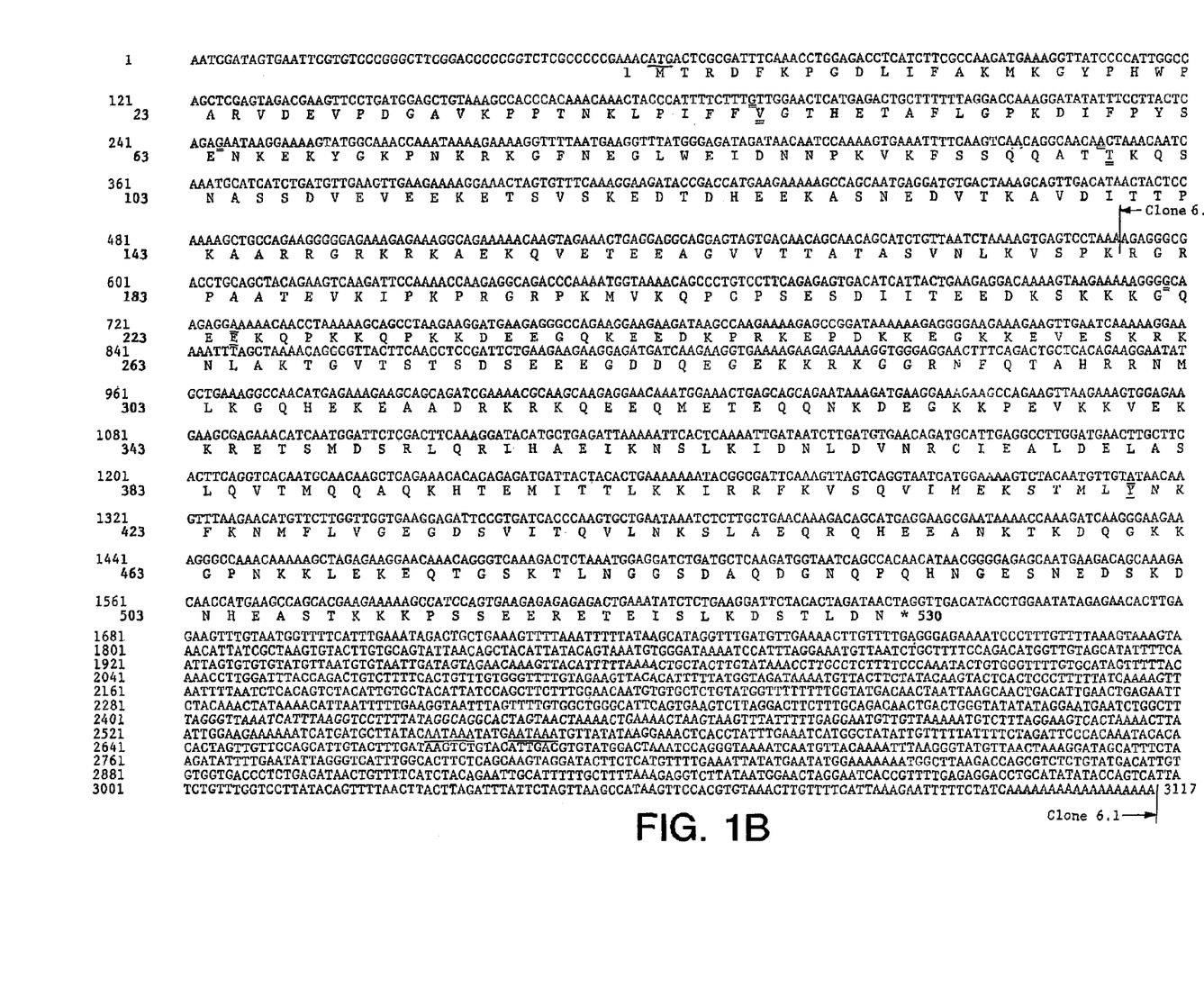

To characterize DFS70 and to determine whether or not it was a novel protein recognized by the sera of both AD and IC patients, we used the more abundant serum from IC patient 90-49 to clone the partial cDNA of DFS70. We first isolated poly A(+) RNA from human T24 bladder epithelial cells and from this starting material a cDNA expression library was constructed, screened with serum, and the positive clones obtained were subeloned and purified to homogeneity. Clone DFS6.1, containing a 2 kb insert, was then cloned and sequenced (FIG. 1A). Analysis of this sequence showed an open reading frarne (ORF) of approximately 1 kb, coding for 351 amino acids with a predicted molecular weight of 40 kDa (FIG. 1B). A search of the gene sequence database at that time indicated no identity with previously reported sequences. The sequence of cDNA clone DFS6.1 from protein DFS70 was deposited in GenBank under accession #U94319 (Ochs et al., *Molec Biol Cell* 1995; 6.75a Suppl.) in 1997.

An overlapping clone #52 was obtained from human placental cDNAs using 5'RACE (FIG. 1A). Independent confirmation was provided from RT-PCR using primers upstream of the methionine start and translation stop codons. The amplified cDNA was subdloned into pET28 for sequencing analysis as described herein above. The complete cDNA and deduced amino acid sequences are shown in FIG. 1B. GenBank search at this time showed that DFS70 was identical to transcription coactivator p75 (Ge et al., *EMBO J* 1998; 17:6723-6729) and lens epithelium-derived growth factor (LEDGF) (Singh et al., *Invest Ophthalmol Vis Sci* 1998; 39:2132-9). The two to four amino acid differences among these proteins (see FIG. 1B) may reflect errors in reverse transcriptase function during the cDNA synthesis step for establishing the cDNA expression libraries since these are single nucleotide differences. It should be noted that different cell lines, T24 in this report, HeLa (Ge et al., *EMBO J.* 1998; 17:6723-6729) and lens epithelial cell (Singh et al., *Invest Ophthalmol Vis Sci* 1998; 39:2132-9 (Abst)) cDNA libraries were used for isolating the different cDNA clones.

Western Blotting: A Shiared Autoantibody/Autoantigen System in AD and IC Patients For a higher level of protein expression and to purify the recombinant protein away from contaminating bacterial proteins that might interfere in Western blotting, the full-length cDNA clone of DFS70 was excised and cloned into pET vector 28a (pET-DFS) that has a 5' T7 fusion protein tag and a 6× histidine tag. Recombinant DFS70 protein expressed from clone pET-DFS was bound and specifically eluted from a nickel affinity column and was detected with either T7 antibody or the serum from IC patient 90-49 used to originally isolate clone 6.1 of DFS70. Purified recombinant DFS70 was then used to confirm the presence of IgG antibodies originally detected using MOLT-4 cell extracts. Patients that were positive in Western blotting against a 70 kDa protein contained in MOLT-4 cells and were also positive against recombinant DFS70. All 64 AD sera were subsequently examined in Western blotting against recombinant DFS70 and 19 (29.6%) were positive (see Table 2).

TABLE 2

Patient Groups Reactive with Recombinant DFS70 by Western Blotting

| Patients | Reactivity |
| --- | --- |
| Normal Controls | 0/39 (0%) |
| Atopic Dermatitis | 19/64 (29.6%) |
| Asthma | 8/50 (16%) |
| Interstitial Cystitis | 9/103 (8.7%) |
| Psoriasis | 1/22 (4.5%) |
| Chronic Fatigue Syndrome | 2/60 (3.3%) |
| Systemic Lupus Erythematosus | 0/36 (0%) |
| Rheumatoid Arthritis | 0/30 (0%) |
| Sjögren's Syndrome | 2/29 (6.9%) |
| Scleroderma | 1/40 (2.5%) |

In summary, of 18 sera showing putative DFS staining patern by immunohistochemistry, 14 were positive in Western blotting against recombinant DFS70 and of the 46 AD sera without this pattern in immunohistochemistry, 5 were positive in Western blotting.

The IgG subclass was determined for 16 AD sera that were reactive for DFS70. All antibodies were of the IgG1 subclass and none were IgG4. Two sera also contained antibodies of the IgG2 subclass and 3 others contained antibodies of the IgG3 subclass.

Detection of IgE Autoantibodies to DFS70

Since blood levels of IgE are approximately 100,000 times less than those for IgG, we performed IgE Western blotting at serum dilution of ¹/₁₀ compared to normal dilutions of ¹/₁₀₀ for IgG, and the signals obtained also necessitated much longer autoradiographic exposure times (20 minutes for IgE antibody versus 5 seconds for IgG antibody). In both IC and Ad patients we could detect specific IgE autoantibodies to DFS70 by Western blotting. It was noted that in general, there was a positive relationship between signals for IgG and for IgE antibodies in that a strong signal for IgG antibody correlated with a strong signal for IgE antibody.

Other Patient Groups Reactive with Recombinant DFS70

Table 2 summarizes the results of Western blotting against recombinant DFS 70 protein in various groups of patients and normal controls. None of the normal healthy controls were positive for IgG autoantibodies reactive with recombinant DFS70 compared to 30% of AD patients. This result compares with a positivity of 16% for asthma patients, 8.7% for IC, 4.5% for psoriasis patients, 3.3% for patients diagnosed with chronic fatigue syndrome, 0% for lupus patients, 0% for rheumatoid arthritis patients, 6.9% for Sjögren's patients, and 2.5% for patients with scleroderma.

Human Autoantibodies to DFS70 Bind Transcription Coactivator p75, but not p52

During the course of the studies described above, a report by Ge et al. (Ge et al., *EMBO J.* 1998; 17:6723-6729) described the isolation of cDNAs encoding transcription coactivators p52 and p75, which these authors showed were required for transcriptional activation in human cell-free systems containing RNA polymerase It and general initiation factors. p52 is a protein of 333 aa and is a splice variant of a gene that also encodes a protein p75 of 530 aa with the additional amino acids of p75 located in the C-terminal region. Our initial DFS6.1 partial cDNA clone encoded for the C-terminal 351 aa of p75 and it was of interest to determine how AD sera reacted with the splice variants p75 and p52. Five human sera, four from patients with atopic dermatitis (LB, KK,CK, WS) and an autoimmune serum containing autoantibodies to other cellular antigens were coded and analyzed for reactivity in the Ge laboratory with the upstream stimulatory activity (USA) fraction of HeLa cells which contained both p52 and p75. All the atopic dermatitis sera reacted with p75 but not with p52 whereas the irrelevant autoimmune serum AF reacted with USA fraction to give two unrelated bands of unknown identity. Rabbit antibodies raised against p52 and p75 fractions were used as positive controls: anti-p52 reacted with both p52 and p75 whereas anti-p75 reacted with p75 alone. This could be expected since anti-p52 was raised with full-length p52 as immunogen whereas anti-p75 was raised with the unique C-terminal region of p75. The human sera were further analyzed in Western blotting with recombinant p75 and p52, with the results confirming the observations made with the USA fraction.

Rabbit Antibodies to Recombinant p75 and p52 Bind to Recombinant DFS70 and Display DFS Localization It was demonstrated that rabbit antibodies raised against recombinant transcription factors p75 and p52 were both able to bind to recombinant full-length DFS70. When the rabbit antibodies were used in immunohistochemistry, they displayed identical patterns of immunolocalization as compared to human anti-DFS70. A pattern of dense fine speckles in interphase nuclei and generalized staining of condensed chromosomes in mitotic nuclei was observed.

Localization of DFS70 at the Ultrastructural Level

A high titered human anti-DFS70 was selected for immunoelectron microscopy and the targets were small pieces of mouse intestine fixed at 4° C. with 1% glutaraldehyde as described in Materials and Methods. Mouse intestine was used as the substrate because p75 has been shown to be ubiquitously expressed at the mRNA level in many different tissues including small intestine (Ge et al., *EMBO J.* 1998; 17:6723-6729) and numerous studies have shown that human autoantibodies react with cellular antigens which are highly conserved between mouse and man (Tan, *Cell* 1991; 67:841-842). Immunoelectron microscopy demonstrated that DFS70/p75 was localized in interphase chromatin and appeared to be concentrated over areas of condensed chromatin in the periphery of the nucleus and also in perinucleolar chromatin. The nucleolus and the interchromatin regions contained relatively few colloidal gold particles.

As shown in Table 1, 18 AD patients had what appeared to be a characteristic DFS staining pattern by immunohistochemistry, but four of these sera (16,77,78,99) were negative in Western blotting against recombinant DFS70. It is possible that if these four sera did have antibodies to DFS70/p75 transcription coactivator, the epitope(s) recognized by the four sera might not be primary sequence regions of the protein but are conformation-dependent epitopes which are lost during denaturation in the polyacrylamide gel electrophoresis-Western blotting procedure. Alternatively, immunohistochemistry might be more sensitive than immunoblotting for this antigen-antibody system. It is also of interest that five AD patients which did not display the prototypic DFS70 staining pattern were found to have antibody to recombinant DFS70 in Western blotting.

The DFS70/p75 autoantibody/autoantigen system showed the highest prevalence in three disease conditions, i.e., atopic dermatitis (30%), asthma (16%) and interstitial cystitis (9%). It has been well documented that AD is frequently associated with bronchial asthma and that children with AD are more likely to develop asthma in later life than non-AD children (Cooper, *J Invest Dermatol* 1994; 102:128-137; Beltrani, *J Allergy Clin Immunol* 1999; 104:S87-S98). In addition to the fact that ANAs are present in higher than normal frequency in IC patients, there are several reports that allergic disorders are a major symptom complaint in IC. In a recent study on 374 patients, food allergies were reported in 25.1% and hay fever in 24.9% (Kozial et al., *J Urol* 1993; 149:465-469). Earlier studies have also pointed out the common occurrence of allergic disorders in IC and the role played by mast cells (Messing, et al. *Urology* 12:381-392; Hanno et al., *J Urol* 1990; 143:278-281). None of these studies reported on the frequency of atopic dermatitis and it might be possible that in IC, some of the patients with allergic diathesis might also have AD and that this could be a common thread running through the three different disease conditions.

It is of interest that the putative function of the DFS70/p75 antigen has been reported to be a transcription co-activator (Ge et al., *EMBO J.* 1998; 17:6723-6729). There are two isoforms which are spliced products of the same gene and encode for p75 as well as a truncated p52 kilodalton protein which lacks the C-termninal region of p75. In studies showing that both these proteins functioned as transcription co-activators in an in vitro transcription system dependent on RNA polymerase II and general transcription factors, the shorter isoform p52 was more active for most activation domains compared to p75. Human autoantibodies recognized exclusively the p75 isoform, indicating that the epitope was located in the C-terminal region of p75 which is absent in p52. We and others have advanced the concept that spontaneously occurring autoantibodies are antigen-driven (Tan, *The Immunologist* 1999; 7:85-92; Radic et al., *Ann Rev Immunol* 1994; 12:487-520) and if this is the case for the autoimmune response to DFS70, the immunogen which is driving the immune reactin is the larger isoform, p75. At the present time, the significance of this finding is unknown, but although p75 is a less active transcription co-activator, it is possible that its involvement in transcription might be related to certain specific activation domains which were not used in the reported studies (Ge et al., *EMBO J.* 1998; 17:6723-6729). In this respect, future studies could address the question whether p75 might enhance transcription activity for certain genes predisposing to the development of atopy (Forrest et al., *J Allergy Clin Immunol* 1999; 104:1066-1070).

Our studies using autoantibodies from patients with AD and IC, and antibodies from rabbits immunized with p75 show that DFS70/p75 is localized in the nucleoplasm by immunohistochemistry. This is consistent with the function of p75 as a transcription co-activator associated with RNA pol II. Immunoelectron microscopy studies also show that DFS70 is localized in the nucleus and preferentially in heterochromatin areas. This is in contrast to the reports by Singh et al. (Singh et al., *Invest Ophthalmol Vis Sci* 1999; 40:1444-1451) on the same protein which they call lens epithelium derived growth factor (LEDGF) which was initially reported to be a cytoplasmic protein (Singh et al., *Invest Ophthalmol Vis Sci* 1998; 39:3590 (Abst)) and subsequently reported to be present in the cytoplasm of lens epithelial cells at 4°, 15° and 28° and in the nucleus and nucleolus at 37° (Singh et al., *Invest Ophthalmol Vis Sci* 1999; 40:1444-1451). Its localization in the cytoplasm at temperatures lower than 37° is non-physiological and the significance of this is unknown. These authors identified LEDGF and isolated a cDNA encoding this protein with the serum of a patient with age-related cataract. Some of the sera from patients with age-related cataract appeared to contain antibodies to LEDGF. The interesting feature is that cataracts and other ocular complications have been reported in certain patients with AD (Nakano et al., *J Jpn Ophthalmol Soc* 1997; 101:64-68; Fagerholm et al., *Graefes Arch Clin Ophthalmol* 1984; 221:149-152) and in one report, lens opacities were noted in 23.8% of 133 eyes examined (Nakano et al., *J Jpn Ophthalmol Soc* 1997; 101:64-68).

We have proposed the notion that spontaneously occurring autoantibodies might be regarded as messengers from the immune system that report abnormal events which involve cellular components participating in disease-related mechanisms and that these cellular components might be the antigens driving the immune response (Tan, *The Immunologist* 1999; 7:85-92). The autoantibodies themselves might not be playing a pathogenic role, but can be used to identify the cellular components participating in such disease processes. However, the question which needs to be addressed is whether the autoimune process in AD involving DFS70/p75 is playing any role in pathogenesis. The current study does not address the question of the cell mediated immune system since cellular infiltrates consisting of increased numbers of lymphocytes, monocytes, macrophages and mast cells are present in atopic lesions (Cooper, *J Invest Dermatol* 1994; 102:128-137; Leung, *J Allergy Clin Immunol* 1999; 104:S99-S108). An important study would be examination of slin biopsies from AD lesions to determine whether there might be abnormal expression of DFS70/p75 mRNA and protein. Such studies could not be done since the present work was carried out only with serum specimens and further studies along these lines are needed. We did find IgE autoantibodies to DFS70/p75 in both AD and IC patients and this finding lends some support to the possible pathogenic significance of the present findings in view of several studies showing prominence of IgE positive Langerhans cells in AD lesions (Leung, *J Allergy Clin Immunol* 1999; 104:S99-S108).

What is claimed is:

1. A process of screening a patient for atopic dermatitis comprising determining in sera of the patient the presence of antibodies against an antigen comprising a nuclear transcription co-activator p75, wherein the presence of said antibodies indicates atopic dermatitis.

2. The process of claim 1 wherein the patient is asthmatic.

3. The process of claim 1 wherein the patient has interstitial cystitis.

4. The process of claim 1 wherein the sera from the patient is contacted with and maintained for a period of time sufficient for formation of an immune complex between antibodies in the sera and the antigen.

5. The process of claim 1 wherein the antibodies are IgG molecules.

6. The process of claim 1 wherein the antibodies are IgE molecules.

* * * * *

SEQUENCE LISTING

<160> NUMBER OF SEQ ID NOS: 4

<210> SEQ ID NO 1
<211> LENGTH: 3117
<212> TYPE: DNA
<213> ORGANISM: Homo sapien
<220> FEATURE:
<221> NAME/KEY: CDS
<222> LOCATION: (56)...(1648)

```
<400> SEQUENCE: 1
aatcgatagt gaattcgtgt cccgggcttc ggaccccggg tctcgccccc gaaac atg         58
                                                                  Met
                                                                  1 act cgc gat ttc aaa cct gga gac ctc atc ttc gcc aag atg aaa ggt        106
Thr Arg Asp Phe Lys Pro Gly Asp Leu Ile Phe Ala Lys Met Lys Gly
          5                   10                  15 tat ccc cat tgg cca gct cga gta gac gaa gtt cct gat gga gct gta        154
Tyr Pro His Trp Pro Ala Arg Val Asp Glu Val Pro Asp Gly Ala Val
             20                  25                  30 aag cca ccc aca aac aaa cta ccc att ttc ttt gtt gga act cat gag        202
Lys Pro Pro Thr Asn Lys Leu Pro Ile Phe Phe Val Gly Thr His Glu
 35                  40                  45 act gct ttt tta gga cca aag gat ata ttt cct tac tca gag aat aag        250
Thr Ala Phe Leu Gly Pro Lys Asp Ile Phe Pro Tyr Ser Glu Asn Lys
 50                  55                  60                  65 gaa aag tat ggc aaa cca aat aaa aga aaa ggt ttt aat gaa ggt tta        298
Glu Lys Tyr Gly Lys Pro Asn Lys Arg Lys Gly Phe Asn Glu Gly Leu
                 70                  75                  80 tgg gag ata gat aac aat cca aaa gtg aaa ttt tca agt caa cag gca        346
Trp Glu Ile Asp Asn Asn Pro Lys Val Lys Phe Ser Ser Gln Gln Ala
             85                  90                  95 aca act aaa caa tca aat gca tca tct gat gtt gaa gtt gaa gaa aag        394
Thr Thr Lys Gln Ser Asn Ala Ser Ser Asp Val Glu Val Glu Glu Lys
        100                 105                 110 gaa act agt gtt tca aag gaa gat acc gac cat gaa gaa aaa gcc agc        442
Glu Thr Ser Val Ser Lys Glu Asp Thr Asp His Glu Glu Lys Ala Ser
115                 120                 125 aat gag gat gtg act aaa gca gtt gac ata act act cca aaa gct gcc        490
Asn Glu Asp Val Thr Lys Ala Val Asp Ile Thr Thr Pro Lys Ala Ala
130                 135                 140                 145 aga agg ggg aga aag aga aag gca gaa aaa caa gta gaa act gag gag        538
Arg Arg Gly Arg Lys Arg Lys Ala Glu Lys Gln Val Glu Thr Glu Glu
                150                 155                 160 gca gga gta gtg aca aca gca aca gca tct gtt aat cta aaa gtg agt        586
Ala Gly Val Val Thr Thr Ala Thr Ala Ser Val Asn Leu Lys Val Ser
            165                 170                 175 cct aaa aga ggg cga cct gca gct aca gaa gtc aag att cca aaa cca        634
Pro Lys Arg Gly Arg Pro Ala Ala Thr Glu Val Lys Ile Pro Lys Pro
        180                 185                 190 aga ggc aga ccc aaa atg gta aaa cag ccc tgt cct tca gag agt gac        682
Arg Gly Arg Pro Lys Met Val Lys Gln Pro Cys Pro Ser Glu Ser Asp
195                 200                 205 atc att act gaa gag gac aaa agt aag aaa aag ggg caa gag gaa aaa        730
Ile Ile Thr Glu Glu Asp Lys Ser Lys Lys Lys Gly Gln Glu Glu Lys
210                 215                 220                 225 caa cct aaa aag cag cct aag aag gat gaa gag ggc cag aag gaa gaa        778
Gln Pro Lys Lys Gln Pro Lys Lys Asp Glu Glu Gly Gln Lys Glu Glu
                230                 235                 240 gat aag cca aga aaa gag ccg gat aaa aaa gag ggg aag aaa gaa gtt        826
Asp Lys Pro Arg Lys Glu Pro Asp Lys Lys Glu Gly Lys Lys Glu Val
            245                 250                 255 gaa tca aaa agg aaa aat tta gct aaa aca ggg gtt act tca acc tcc        874
Glu Ser Lys Arg Lys Asn Leu Ala Lys Thr Gly Val Thr Ser Thr Ser
        260                 265                 270 gat tct gaa gaa gaa gga gat gat caa gaa ggt gaa aag aag aga aaa        922
Asp Ser Glu Glu Glu Gly Asp Asp Gln Glu Gly Glu Lys Lys Arg Lys
275                 280                 285
```

-continued

| | |
|---|---|
| ggt ggg agg aac ttt cag act gct cac aga agg aat atg ctg aaa ggc<br>Gly Gly Arg Asn Phe Gln Thr Ala His Arg Arg Asn Met Leu Lys Gly<br>290                        295                      300                      305 | 970 |
| caa cat gag aaa gaa gca gca gat cga aaa cgc aag caa gag gaa caa<br>Gln His Glu Lys Glu Ala Ala Asp Arg Lys Arg Lys Gln Glu Glu Gln<br>                    310                      315                      320 | 1018 |
| atg gaa act gag cag cag aat aaa gat gaa gga aag aag cca gaa gtt<br>Met Glu Thr Glu Gln Gln Asn Lys Asp Glu Gly Lys Lys Pro Glu Val<br>325                        330                      335 | 1066 |
| aag aaa gtg gag aag aag cga gaa aca tca atg gat tct cga ctt caa<br>Lys Lys Val Glu Lys Lys Arg Glu Thr Ser Met Asp Ser Arg Leu Gln<br>                    340                      345                      350 | 1114 |
| agg ata cat gct gag att aaa aat tca ctc aaa att gat aat ctt gat<br>Arg Ile His Ala Glu Ile Lys Asn Ser Leu Lys Ile Asp Asn Leu Asp<br>355                        360                      365 | 1162 |
| gtg aac aga tgc att gag gcc ttg gat gaa ctt gct tca ctt cag gtc<br>Val Asn Arg Cys Ile Glu Ala Leu Asp Glu Leu Ala Ser Leu Gln Val<br>370                        375                      380                      385 | 1210 |
| aca atg caa caa gct cag aaa cac aca gag atg att act aca ctg aaa<br>Thr Met Gln Gln Ala Gln Lys His Thr Glu Met Ile Thr Thr Leu Lys<br>                    390                      395                      400 | 1258 |
| aaa ata cgg cga ttc aaa gtt agt cag gta atc atg gaa aag tct aca<br>Lys Ile Arg Arg Phe Lys Val Ser Gln Val Ile Met Glu Lys Ser Thr<br>405                        410                      415 | 1306 |
| atg ttg tat aac aag ttt aag aac atg ttc ttg gtt ggt gaa gga gat<br>Met Leu Tyr Asn Lys Phe Lys Asn Met Phe Leu Val Gly Glu Gly Asp<br>                    420                      425                      430 | 1354 |
| tcc gtg atc acc caa gtg ctg aat aaa tct ctt gct gaa caa aga cag<br>Ser Val Ile Thr Gln Val Leu Asn Lys Ser Leu Ala Glu Gln Arg Gln<br>435                        440                      445 | 1402 |
| cat gag gaa gcg aat aaa acc aaa gat caa ggg aag aaa ggg cca aac<br>His Glu Glu Ala Asn Lys Thr Lys Asp Gln Gly Lys Lys Gly Pro Asn<br>450                        455                      460                      465 | 1450 |
| aaa aag cta gag aag gaa caa aca ggg tca aag act cta aat gga gga<br>Lys Lys Leu Glu Lys Glu Gln Thr Gly Ser Lys Thr Leu Asn Gly Gly<br>                    470                      475                      480 | 1498 |
| tct gat gct caa gat ggt aat cag cca caa cat aac ggg gag agc aat<br>Ser Asp Ala Gln Asp Gly Asn Gln Pro Gln His Asn Gly Glu Ser Asn<br>485                        490                      495 | 1546 |
| gaa gac agc aaa gac aac cat gaa gcc agc acg aag aaa aag cca tcc<br>Glu Asp Ser Lys Asp Asn His Glu Ala Ser Thr Lys Lys Lys Pro Ser<br>                    500                      505                      510 | 1594 |
| agt gaa gag aga gag act gaa ata tct ctg aag gat tct aca cta gat<br>Ser Glu Glu Arg Glu Thr Glu Ile Ser Leu Lys Asp Ser Thr Leu Asp<br>515                        520                      525 | 1642 |
| aac tag gttgacatac ctggaatata gagaacactt gagaagtttg taatggtttt<br>Asn *<br>530 | 1698 |
| catttgaaat agactgctga agttttaaa tttttataag cataggtttg atgttgaaaa | 1758 |
| cttgttttga gggagaaaat ccctttgttt taaagtaaag taaacattat cgctaagtgt | 1818 |
| acttgtcag tattaacagc tacattatac agtaaatgtg ggatggaatc catttaggaa | 1878 |
| atgttaaact gcttttccag acatggttgt agcatatttt caattagtgt gtgtatgtta | 1938 |
| atgtgtaatt gatagtagaa caaagttaca tttttaaaac tgctacttgt ataaaccttg | 1998 |
| cctcttttcc caaatactgt gggttttgtg catagttttt acaaaccttg gatttaccag | 2058 |
| actgtctttt cactgtttgt gggttttgta gaagttacac attttatgg tagataaaat | 2118 |
| gttacttcta tacaagtact cactcccttt ttatcaaaag ttaattttaa tctcacagtc | 2178 |

```
tacattgtgc tacattatcc agcttctttg gaacaatgtg tgctctgtat ggttttttt      2238 ggtatgacaa ctaattaagc aactgacatt gaactgagaa ttctacaaac tataaaacat      2298 taattttga aggtaattta gttttgtggc tgggcattca gtgaagtctt aggacttctt      2358
tgcagacaac tgactgggta tatataggaa tgaatctggc tttagggtta aatcatttaa      2418 ggtccttta taggcaggca ctagtaacta aaactgaaaa ctaagtaagt ttattttga      2478 ggaatgttgt taaaaatgtc tttaggaagt cactaaaact taattggaag aaaaaatcat      2538
gatgcttata caataaatat gaataaatgt tatataagga aactcaccta tttgaaatca      2598
tggctatatt gttttatt tctagattcc cacaaataca cacactagtt gttccagcat      2658
tgtactttga taagtctgta cattgacgtg tatggactaa atccaggta aaatcaatgt      2718 tacaaaattt aagggtatgt taactaaagg atagcatttc taagatattt tgaatattag      2778
ggtcatttgg cacttctcag caagtaggat acttctcatg ttttgaaatt atatgaatat      2838 ggaaaaaat ggcttaagac cagcgtctct gtatgacatt gtgtggtgac cctctgagat      2898 aactgtttc atctacagaa ttgcatttt gcttttaaag aggtcttata atggaactag      2958
gaatcaccgt tttgagagga cctgcatata taccagtcat tatctgtttg gtccttatac      3018
agttttaact tacttagatt tattctagtt aagccataag ttccacgtgt aaacttgttt      3078
tcattaaaga atttttctat caaaaaaaaa aaaaaaaa                              3117

<210> SEQ ID NO 2
<211> LENGTH: 530
<212> TYPE: PRT
<213> ORGANISM: Homo sapien

<400> SEQUENCE: 2

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Val Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
65                  70                  75                  80

Leu Trp Glu Ile Asp Asn Asn Pro Lys Val Lys Phe Ser Ser Gln Gln
                85                  90                  95

Ala Thr Thr Lys Gln Ser Asn Ala Ser Ser Asp Val Glu Val Glu Glu
            100                 105                 110

Lys Glu Thr Ser Val Ser Lys Glu Asp Thr Asp His Glu Glu Lys Ala
        115                 120                 125

Ser Asn Glu Asp Val Thr Lys Ala Val Asp Ile Thr Thr Pro Lys Ala
    130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                165                 170                 175

Ser Pro Lys Arg Gly Arg Pro Ala Ala Thr Glu Val Lys Ile Pro Lys
            180                 185                 190

Pro Arg Gly Arg Pro Lys Met Val Lys Gln Pro Cys Pro Ser Glu Ser
        195                 200                 205
```

-continued

| | | | | | | | | | | | | |
|---|---|---|---|---|---|---|---|---|---|---|---|---|
|Asp|Ile|Ile|Thr|Glu|Glu|Asp|Lys|Ser|Lys|Lys|Gly|Gln|Glu|Glu|
| |210| | | |215| | | |220| | | | | |
|Lys|Gln|Pro|Lys|Lys|Gln|Pro|Lys|Lys|Asp|Glu|Glu|Gly|Gln|Lys|Glu|
|225| | | | |230| | | | |235| | | | |240|
|Glu|Asp|Lys|Pro|Arg|Lys|Glu|Pro|Asp|Lys|Lys|Glu|Gly|Lys|Lys|Glu|
| | | | |245| | | | |250| | | | |255| |
|Val|Glu|Ser|Lys|Arg|Lys|Asn|Leu|Ala|Lys|Thr|Gly|Val|Thr|Ser|Thr|
| | | |260| | | | |265| | | | |270| | |
|Ser|Asp|Ser|Glu|Glu|Gly|Asp|Asp|Gln|Glu|Gly|Glu|Lys|Lys|Arg|
| | |275| | | | |280| | | | |285| | |
|Lys|Gly|Gly|Arg|Asn|Phe|Gln|Thr|Ala|His|Arg|Arg|Asn|Met|Leu|Lys|
| |290| | | | |295| | | | |300| | | | |
|Gly|Gln|His|Glu|Lys|Glu|Ala|Ala|Asp|Arg|Lys|Arg|Lys|Gln|Glu|Glu|
|305| | | | |310| | | | |315| | | | |320|

```
Asp Ile Ile Thr Glu Glu Asp Lys Ser Lys Lys Gly Gln Glu Glu
    210             215             220
Lys Gln Pro Lys Lys Gln Pro Lys Lys Asp Glu Glu Gly Gln Lys Glu
225             230             235             240
Glu Asp Lys Pro Arg Lys Glu Pro Asp Lys Lys Glu Gly Lys Lys Glu
            245             250             255
Val Glu Ser Lys Arg Lys Asn Leu Ala Lys Thr Gly Val Thr Ser Thr
        260             265             270
Ser Asp Ser Glu Glu Gly Asp Asp Gln Glu Gly Glu Lys Lys Arg
    275             280             285
Lys Gly Gly Arg Asn Phe Gln Thr Ala His Arg Arg Asn Met Leu Lys
    290             295             300
Gly Gln His Glu Lys Glu Ala Ala Asp Arg Lys Arg Lys Gln Glu Glu
305             310             315             320
Gln Met Glu Thr Glu Gln Gln Asn Lys Asp Glu Gly Lys Lys Pro Glu
            325             330             335
Val Lys Lys Val Glu Lys Lys Arg Glu Thr Ser Met Asp Ser Arg Leu
        340             345             350
Gln Arg Ile His Ala Glu Ile Lys Asn Ser Leu Lys Ile Asp Asn Leu
        355             360             365
Asp Val Asn Arg Cys Ile Glu Ala Leu Asp Glu Leu Ala Ser Leu Gln
    370             375             380
Val Thr Met Gln Gln Ala Gln Lys His Thr Glu Met Ile Thr Thr Leu
385             390             395             400
Lys Lys Ile Arg Arg Phe Lys Val Ser Gln Val Ile Met Glu Lys Ser
            405             410             415
Thr Met Leu Tyr Asn Lys Phe Lys Asn Met Phe Leu Val Gly Glu Gly
            420             425             430
Asp Ser Val Ile Thr Gln Val Leu Asn Lys Ser Leu Ala Glu Gln Arg
            435             440             445
Gln His Glu Glu Ala Asn Lys Thr Lys Asp Gln Gly Lys Lys Gly Pro
    450             455             460
Asn Lys Lys Leu Glu Lys Glu Gln Thr Gly Ser Lys Thr Leu Asn Gly
465             470             475             480
Gly Ser Asp Ala Gln Asp Gly Asn Gln Pro Gln His Asn Gly Glu Ser
            485             490             495
Asn Glu Asp Ser Lys Asp Asn His Glu Ala Ser Thr Lys Lys Lys Pro
            500             505             510
Ser Ser Glu Glu Arg Glu Thr Glu Ile Ser Leu Lys Asp Ser Thr Leu
        515             520             525
Asp Asn
    530
```

<210> SEQ ID NO 3
<211> LENGTH: 29
<212> TYPE: DNA
<213> ORGANISM: Artificial Sequence
<220> FEATURE:
<223> OTHER INFORMATION: synthesized

<400> SEQUENCE: 3
gcagaattcg atacatgact cgcgatttc                                      29

```
-continued

<210> SEQ ID NO 4
<211> LENGTH: 36
<212> TYPE: DNA
<213> ORGANISM: Artificial Sequence
<220> FEATURE:
<223> OTHER INFORMATION: synthesized

<400> SEQUENCE: 4
agtgaagctt atattccagg tatgtcaacc tacgtt                                    36
```